United States Patent

Onodera et al.

[11] Patent Number: 4,524,055
[45] Date of Patent: Jun. 18, 1985

[54] CRYSTALLINE ALUMINOSILICATE ZEOLITE AND PROCESS FOR PRODUCTION THEREOF

[75] Inventors: Tamio Onodera; Tokuji Sakai; Yasuo Yamasaki; Koji Sumitani, all of Matsuyama, Japan

[73] Assignee: Teijin Petrochemical Industries Ltd., Tokyo, Japan

[21] Appl. No.: 468,381

[22] Filed: Feb. 22, 1983

[30] Foreign Application Priority Data

Feb. 22, 1982 [JP] Japan .................................. 57-26000

[51] Int. Cl.³ .......................... C01B 33/28; B01J 29/28
[52] U.S. Cl. ........................................ 423/328; 502/77; 502/85
[58] Field of Search ................... 423/328; 502/60, 77, 502/85

[56] References Cited

U.S. PATENT DOCUMENTS

| | | | |
|---|---|---|---|
| 3,483,137 | 12/1969 | Sensel | 423/328 X |
| 3,702,886 | 11/1972 | Argauer et al. | 423/328 |
| 3,766,093 | 10/1973 | Chu | 502/60 X |
| 3,849,463 | 11/1974 | Dwyer et al. | 423/328 X |
| 4,134,965 | 1/1979 | Rein et al. | 423/328 |
| 4,187,283 | 2/1980 | Kokotailo et al. | 502/85 |
| 4,263,129 | 4/1981 | Chen et al. | 208/111 |

Primary Examiner—Edward J. Meros

[57] ABSTRACT

A novel crystalline aluminosilicate zeolite characterized by having (a) a silica/alumina mole ratio in the range of from 10 to 100,
(b) X-ray lattice distances d shown in Table A in the specification, and
(c) a (cyclohexane/n-hexane) adsorption ratio of at least 0.7. This crystalline aluminosilicate zeolite is useful, for example, as a catalyst in the isomerization reaction or transalkylation reaction of alkylbenzenes or alkylnaphthalenes, and can be prepared by heating a crystalline aluminosilicate zeolite ZSM-5 having a silica/alumina mole ratio of from 20 to 300 at a temperature between 80° C. and 250° C. in an aqueous solution containing 0.1 to 1 g, per gram of the ZSM-5 zeolite, of an alkali metal hydroxide.

9 Claims, 2 Drawing Figures

CRYSTALLINE ALUMINOSILICATE ZEOLITE AND PROCESS FOR PRODUCTION THEREOF

This invention relates to a novel crystalline aluminosilicate zeolite, and more specifically, to a novel crystalline aluminosilicate zeolite which is produced by modifying a synthetic crystalline aluminosilicate zeolite and has different X-ray diffraction characteristics, adsorption characteristics and chemical characteristics from zeolite ZSM-5, a process for its production, and its use as a catalyst.

Unless otherwise specified, the crystalline aluminosilicate zeolite will sometimes be referred to simply as "zeolite" in the present specification.

Zeolites are characterized by containing a cation such as a Na, K or H ion and having a three-dimensional network crystalline structure composed principally of $SiO_4$ and $AlO_4$ in which regular tetrahedrons composed of Si atoms and Al atoms crosslinked through oxygen atoms are highly oriented. They occur naturally or are synthesized.

Zeolites have a uniform size and contain numerous pores. By utilizing these characteristics, they are used as molecular sieves and also find extensive use as catalysts or carriers in various chemical syntheses.

Since synthetic zeolites are very uniform and highly pure and have various desirable excellent properties, many synthetic zeolites and processes for their production have been proposed heretofore.

Zeolites having a high silica content as shown by an $SiO_2/Al_2O_3$ mole ratio of at least 10 have high stability and a unique acidity, and exhibit high activity when used as catalysts for conversion of hydrocarbons, for example their selective adsorption, cracking, hydrocracking, isomerization, alkylation, etc. Many such zeolites having a high silica content, mainly ZSM series zeolites, have been proposed up to date (see, for example, U.S. Pat. Nos. 3,702,886; 3,709,979; 3,832,449; 4,016,245 and 4,061,724.).

Zeolites having a high silica content are produced usually by reacting a silica source, an alumina source, an alkali metal cation and another cation to be used in combination with it, and the structure and properties of the resulting zeolites differ depending upon the kind and combination of the other cation.

Heretofore, many proposals have been made to use specified amines or organic ammonium salts as the other cation to be used in combination with the alkali metal cation (see, for example, British Pat. No. 2,018,232, West Germany Patent Publication No. 2924915, European Patent Publication Nos. 2899 and 2890.).

However, zeolites synthesized and used commercially are limited in species, and among them, ZSM series zeolites, particularly ZSM-5, are produced and used in great quantities because of their excellent activity and stability.

As described in detail in U.S. Pat. No. 3,702,886, ZSM-5 is synthesized by the presence of an alkali metal cation (specifically, a sodium ion) and a specified organic ammonium ion (specifically, a tetrapropyl ammonium ion). The ZSM-5 so produced is highly crystalline and has a high silica/alumina mole ratio and the characteristic X-ray lattice distances described in the aforesaid patent specification. ZSM-5 has many uniform pores of a definite size, and this partly characterizes the properties of ZSM-5.

Synthetic zeolites having a definite structure and properties are formed depending upon the combination of the cations used for their production, and ZSM-5 zeolite can be obtained in a definite structure and properties by the manufacturing process described above.

ZSM-5 series would be able to be utilized in a wider area if their structure, especially their pore size, can be changed while maintaining excellent activity, stability and other properties.

The present inventors, therefore, worked extensively on zeolites having substantially the same basic crystal structure as ZSM-5 and contain broadened pores. This research work has led to the discovery that when ZSM-5 is heated at a specified temperature in a specified proportion of an aqueous solution of sodium hydroxide, a novel zeolite can be obtained which has X-ray lattice distances d shown in Table A below which differ from those of ZSM-5, particularly in respect of peaks at $d(Å)=3.86$ and $3.83$, a slightly larger pore size than ZSM-5 and quite unique reaction activity as compared with ZSM-5.

According to this invention, there is provided a novel crystalline aluminosilicate zeolite characterized by having (a) a $SiO_2/Al_2O_3$ mole ratio in the range of from 10 to 100, (b) X-ray lattice distances d shown in Table A below, and (c) a (cyclohexane/n-hexane) adsorption ratio of at least 0.7.

The zeolite of this invention has a high $SiO_2/Al_2O_3$ mole ratio as ZSM-5, but is clearly distinguished from it in lattice distances in X-ray diffraction and (cyclohexane/n-hexane) adsorption characteristics. It also clearly differs from the zeolite described in West Germany Patent Publication No. 2548697, Japanese Laid-Open Patent Publication No. 17920/1981 and European Patent Publication No. 57016, which disclose zeolites similar to ZSM-5 series.

The novel zeolite of this invention will now be described in more detail partly in conjunction with the accompanying drawings in which.

The zeolite of this invention has a $SiO_2/Al_2O_3$ mole ratio in the range of from 10 to 100, preferably 15 to 70, more preferably 20 to 50.

Figure 1:
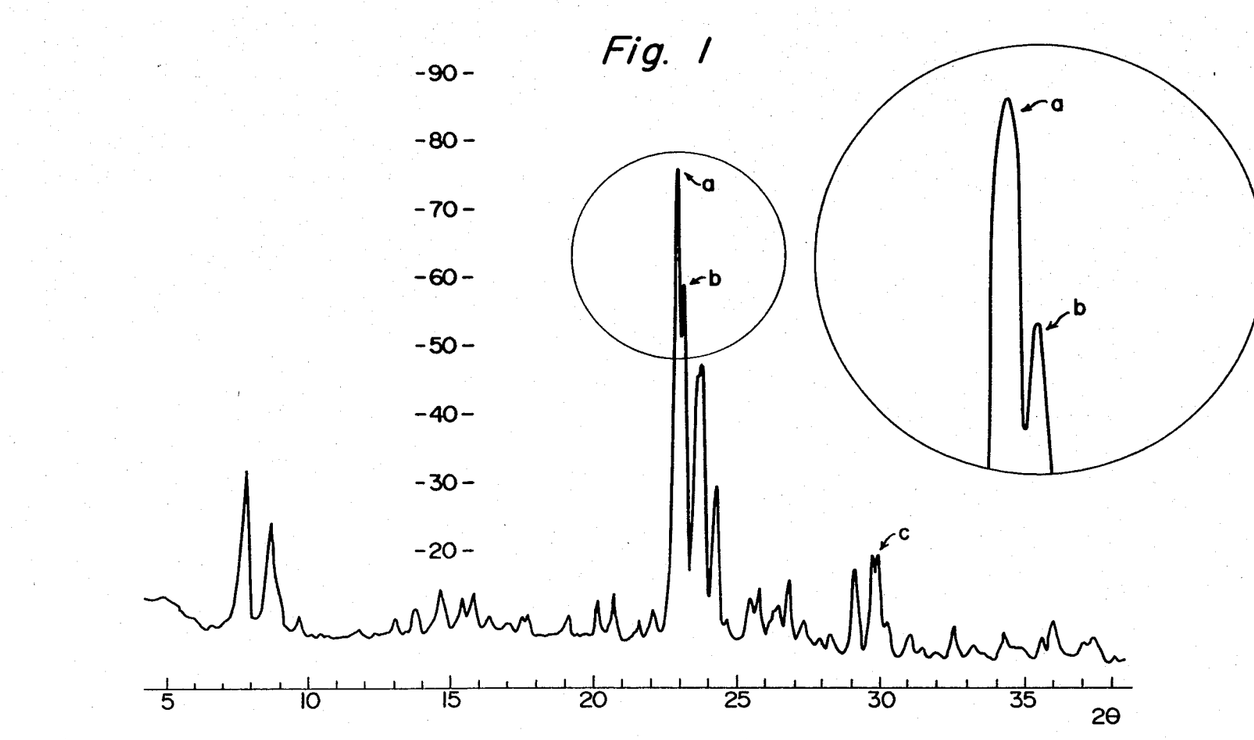
FIG. 1 is an X-ray diffraction chart of a typical zeolite in accordance with this invention.

The zeolite of the invention has the X-ray lattice distances shown in Table A below. The present inventors have found as a result of detailed comparative study that some differences exist between the X-ray diffraction chart of the zeolite of the invention and that of ZSM-5. One great difference is that the X-ray lattice distance $d(Å)$ which gives the strongest peak in ZSM-5 is 3.85 ($2\theta=23.14$) according to the above-cited U.S. Pat. No. 3,702,886, whereas in the zeolite of this invention, the strongest peak is branched and observed at $d(Å)=3.86$ and $3.83$ ($2\theta=23.05$ and $23.25$) (see peaks a and b in FIG. 1). Another great difference is that one peak observed at $d(Å)=3.00$ ($2\theta=29.76$) in ZSM-5 is observed as a bifurcated peak at $d(Å)=3.00$ ($2\theta=29.75$) (peak c of FIG. 1). The latter-mentioned bifurcated peak is observed in most of the zeolites of this invention, if not in all.

The X-ray lattice distances d(Å) of the zeolite of this invention and their relative intensities are shown below. The relative intensity (I/Io) is relative intensity of each peak when the intensity (Io) of a peak at d(Å)=3.86 (2θ=23.05) is taken as 100. The relative intensities [I/Io(%)] are rated as follows:

TABLE A

| X-ray lattice distance, d(Å) | Diffraction angle, 2θ | Relative intensity (I/Io) |
| --- | --- | --- |
| 11.26 | 7.85 | M |
| 10.11 | 8.75 | W–M |
| 9.83 | 9.00 | W |
| 9.12 | 9.70 | W |
| 7.51 | 11.80 | W |
| 6.78 | 13.05 | W |
| 6.05 | 14.65 | W–M |
| 5.74 | 15.45 | W |
| 5.61 | 15.80 | W |
| 5.41 | 16.40 | W |
| 5.00 | 17.75 | W |
| 4.65 | 19.10 | W |
| 4.39 | 20.25 | W |
| 4.28 | 20.75 | W–M |
| 4.11 | 21.65 | W–M |
| 4.04 | 22.05 | W |
| 3.86 | 23.05 | VS |
| 3.83 | 23.25 | VS |
| 3.75 | 23.70 | S |
| 3.74 | 23.80 | S |
| 3.66 | 24.30 | M–S |
| 3.61 | 24.65 | W |
| 3.50 | 25.45 | W–M |
| 3.46 | 25.75 | W–M |
| 3.36 | 26.50 | W |
| 3.33 | 26.80 | W–M |
| 3.28 | 27.20 | W |
| 3.26 | 27.35 | W |
| 3.06 | 29.15 | W–M |
| 3.00 | 29.75 | W–M |
| 2.98 | 29.95 | W–M |
| 2.96 | 30.20 | W |

| I/Io (%) | Rating |
| --- | --- |
| 100–60 | VS (very strong) |
| 60–40 | S (strong) |
| 40–20 | M (medium) |
| 20–10 | W (weak) |

Furthermore, the two very strong peaks at d(Å)=3.86 and 3.83 characteristic of the zeolite of this invention has the relationship that when the intensity (Io) of the peak at d(Å)=3.86 (2θ=23.05) is taken as 100, the relative intensity (I/Io) of the peak at d(Å)=3.83 (2θ=23.25) is at least 75, typically 77 to 80.

Another important characteristic of the zeolite of this invention over ZSM-5 and other similar zeolites is that it has an extremely high (cyclohexane/n-hexane) adsorption ratio which is at least 0.7, preferably at least 0.8, more preferably at least 0.9.

The (cyclohexane/n-hexane) adsorption ratio is a value measured in accordance with the definition given hereinafter. ZSM-5 and similar zeolites have a (cyclohexane/n-hexane) adsorption ratio of less than 0.7, and to the best of the knowledge of the present inventors, no ZSM-5 zeolite exists which has a (cyclohexane/n-hexane) adsorption ratio of 0.7 or more. The adsorption ratio is a value which shows the proportion of cyclohexane adsorbed to n-hexane. The higher this value, the larger is the diameter (size) of pores in the zeolite. If the adsorption ratio becomes too high, the zeolite loses selective adsorption characteristics. The upper limit of the adsorption ratio of the zeolite of this invention is generally about 1.3, typically about 1.2, and the zeolite of this invention has a moderate pore diameter.

The novel zeolite of this invention also has unique chemical activity. For example, the novel zeolite in the activated state has a cyclohexane decomposition index ratio (the activity of the zeolite relative to the activity of ZSM-5 having the same $SiO_2/Al_2O_3$ mole ratio when each zeolite is contacted with cyclohexane) of at least 1.1, preferably at least 1.5, more preferably at least 1.7.

The term "in the activated state", as used in the present specification and the appended claims, means that most of alkali metal ions contained in the synthesized zeolite of this invention immediately after preparation are substituted by hydrogen ions in accordance with known methods. In other words, it means that at least 70%, preferably at least 90%, of cation exchange sites based on the alumina of the zeolite are substantially occupied by hydrogen ions, whereby zeolite in the activated state is obtained (the zeolite in this state may sometimes be referred to as "H-form zeolite").

Generally, zeolites have an approximatelly definite activity (especially acidity) according to its $SiO_2/Al_2O_3$ mole ratio. However, the zeolite of the present invention has the characteristic that it has a higher activity than ZSM-5 having nearly the same $SiO_2/Al_2O_3$ mole ratio. If the cyclohexane decomposing activity of a certain standard ZSM-5 is taken as 1, that activity of the zeolite of the invention having nearly the same $SiO_2/Al_2O_3$ mole ratio as the ZSM-5 is shown by a cyclohexane decomposition index ratio of at least 1.1, preferably at least 1.5. The present inventors presume that it is due to the larger pore diameter (size) and the higher acid strength in the pores of the zeolite of this invention than ZSM-5. The upper limit of the cyclohexane decomposition index ratio of the zeolite of this invention is generally 3, preferably 2.5.

The "(cyclohexane/n-hexane) adsorption ratio" and the "cyclohexane decomposition index ratio", which are indices showing the characteristic features of the zeolite of this invention, are defined and measured as described below.

(1) (Cyclohexane/n-hexane) adsorption ratio (to be sometimes abbreviated C.N.A. value):

This value is the ratio of the weight of cyclohexane adsorbed in the weight of n-hexane adsorbed per unit weight of the zeolite. It is a parameter which defines the pore diameter of the zeolite. The larger the C.N.A. value, the more easily molecules having a large cross-sectional area such as cyclohexane molecules diffuse into the pores of the zeolite.

The amount of n-hexane or cyclohexane adsorbed per unit weight of the zeolite is measured as follows: A pelletized zeolite sample calcined at 450° C. for 8 hours in an electric furnace is precisely weighed by means of a spring balance in an adsorption apparatus. Then, the inside of an adsorption tube is evacuated, and cyclohexane or n-hexane in the gaseous state is introduced into the tube until the pressure reaches 60±2 mmHg. The adsorption apparatus is maintained at 20±1° C. for 2 hours. The amount of cyclohexane or n-hexane adsorbed to the zeolite can be measured from the difference in the lengths of the spring balance before and after adsorption.

(2) Cyclohexane decomposition index ratio (to be sometimes abbreviated C.D.R. value hereinafter)

The cyclohexane decomposition index ratio is defined as the ratio of the cyclohexane decomposition index of the H-form zeolite obtained by this invention to that of an H-form ZSM-5 zeolite in the activated state having the same silica/alumina mole ratio as the zeolite of the invention.

The cyclohexane decomposition index is measured by calcining a pelletized zeolite having a size of 10 to 20 mesh and containing 50% by weight of γ-alumina in an electric furnace at 450° C. for 8 hours, loading a predetermined weight of the calcined zeolite in a fixed bed-type reactor, and feeding cyclohexane and hydrogen (hydrogen/cyclohexane mole ratio=2/1) at a temperature of 350° C. and a weight hourly space velocity (WHSV) of 2 hour$^{-1}$ (based on the total weight) under ambient pressure. The amount of cyclohexane converted (per 100 parts by weight of the feed) under these conditions is the cyclohexane decomposition index. WHSV is a value calculated from the following formula.

$$WHSV = \frac{\text{Weight of the hydrocarbon feed fed per unit time}}{\text{Weight of the catalyst}}$$

The novel zeolite of this invention having the aforesaid characteristic features can be produced from ZSM-5 as a raw material by heating crystalline aluminosilicate zeolite ZSM-5 having a silica/alumina mole ratio of 20 to 300 at a temperature of 80° to 250° C. in an aqueous solution containing 0.1 to 1 g, per gram of the zeolite, of an alkali metal hydroxide.

The starting ZSM-5 can be produced by the method described in U.S. Pat. Nos. 3,702,886 and 3,766,093. Advantageously, the ZSM-5 zeolite used in this invention has a silica/alumina mole ratio of 20 to 300, preferably 30 to 200. ZSM-5 zeolite having a silica/alumina mole ratio of less than 20 is difficult to synthesize and is not easy of access. It is surprising that according to the present invention, zeolites having a silica/alumina mole ratio of less than 20 can be easily produced from ZSM-5 zeolite having a silica/alumina mole ratio of at least 20, preferably at least 30, as raw materials, and the zeolites so produced having the aforesaid unique activity.

Examples of the alkali metal hydroxide used for treating the starting zeolite ZSM-5 include sodium hydroxide, potassium hydroxide and lithium hydroxide. Sodium hydroxide is especially preferred. The amount of the alkali metal hydroxide used is 0.1 to 1 g, preferably 0.2 to 0.7 g, more preferably 0.3 to 0.5 g, per gram of the ZSM-5 used.

The starting ZSM-5 zeolite is generally contacted with the alkali metal hydroxide in the form of an aqueous solution. The amount of water used is not critical, and can be varied widely according to the SiO$_2$/Al$_2$O$_3$ mole ratio or amount used of the ZSM-5 and/or to the type or amount used of the alkali metal hydroxide, etc. Usually, the minimum required amount is one sufficient for dipping all of the fed ZSM-5 fully in the aqueous solution. The concentration of the alkali metal hydroxide in the aqueous solution is not critical, and can be varied widely. Generally, it is 1 to 10% by weight, preferably 2 to 7% by weight.

The reaction is carried out by heating the starting ZSM-5 at a temperature of 80° to 250° C., preferably 100° to 200° C.

The reaction can be carried out until a zeolite having the aforesaid characteristics substantially forms. As a measure of its formation, the weight ratio of the zeolite formed to the starting ZSM-5 can be used. Specifically, the reaction can be continued until the weight ratio reaches 10 to 80%, preferably 20 to 70%, more preferably 30 to 60%.

The resulting zeolite has the aforesaid characteristics and has the following chemical composition.

$$xM_{2/n}O \cdot Al_2O_3 \cdot ySiO_2 \qquad (I)$$

This formula represents the zeolite in the form of an oxide in an anhydrous condition. M represents at least one cation having a valence of n, x is 0.5 to 4, and y is 10 to 100.

Immediately after production, M in the zeolite represents an alkali metal, particularly sodium. It can be exchanged with a cation such as a hydrogen ion, an ammonium ion or another metal ion by ion exchange methods usually known. Even the zeolites in accordance with this invention in which M is exchanged with any other cation than a sodium ion essentially have the requirements of the zeolite of the invention described above.

In the formula (I) above, x is a measure of the amount of a cation bonded to the zeolite, and is 0.5 to 4, preferably 0.9 to 3.

A zeolite, i.e. a crystalline aluminosilicate, as a model, consists basically of a combination of tetrahedrons of silica and alumina and has such a structure that the charge of the alumina tetrahedrons is neutralized by the presence of cations in the structures.

Theoretically, therefore, x showing the amount of the cation in formula (I) representing the zeolite is 1 which is equimolar to alumina. In practice, however, synthesized zeolites usually contain cation precursors which cannot be removed by usual washing. It is rare that according to actual analytical data of synthesized zeolites, x becomes 1. Thus, "x" in formula (I) is understood as representing the amount (moles) of total ions in the purified synthetic zeolite which include cations based on alumina, and cation precursors existing in the structure after usual washing.

The zeolite of this invention has X-ray lattice distances different from those of ZSM-5, a slightly larger pore diameter than ZSM-5, and different chemical activity from ZSM-5 (generally the zeolite of the invention has high reaction activity and selectivity for the desired reaction). Hence, it is expected to be used in applications which ZSM-5 zeolite does not find.

Because of the aforesaid excellent properties, the zeolite of this invention can be used widely as a catalyst for the conversion reaction of aromatic hydrocarbons such as the disproportionation, isomerization, alkylation, transalkylation and dealkylation of alkylbenzenes and alkylnaphthalenes, or as a selective adsorbent or as a catalyst carrier.

As a catalyst in these conversion reactions, the zeolite of the invention may be used directly. Depending upon the reaction to be catalyzed, it may also be used after supporting thereon a catalytically active metal or metal oxide which is identical with, or different from, the metal cation present in the cation site. Examples of the catalytically active metals or metal oxides used for this purpose are alkaline earth metals such as magnesium, calcium, strontium and barium, lanthanide metals such as lanthanum and cerium, Group VIII metals in the periodic table such as iron, cobalt, nickel, ruthenium, rhodium, palladium, osmium, iridium and platinum, and the oxides of these.

Such a catalytically active metal or metal oxide may be deposited on the zeolite by methods known per se, for example, by the method described in European Patent Application Specification No. 0018498. Instead of depositing the catalytically active metal or metal oxide on the zeolite of the invention, it is also possible to deposit the metal or metal oxide on a conventional refractory oxide carrier, preferably alumina, mix the supported metal or metal oxide with the zeolite of this invention, mold the mixture into a desired shape such as pellets or tablets, and then used the molded product in the intended reaction.

Since the zeolite of the invention can be advantageously used particularly in the isomerization or transalkylation of alkylbenzenes and alkylnaphthalenes, these reactions will be described below somewhat specifically.

When the zeolite of this invention is used in such isomerization or transalkylation, the zeolite is conveniently one in the activated state in which at least 50%, preferably at least 70%, of the cation sites are occupied by hydrogen ions. In these reactions, the zeolite of the invention may be used in the form of a fine powder, or as required, in the form of pellets, tablets and other desired shaped obtained by molding it in a usual manner. Molding of the zeolite is carried out in a customary manner by mixing it with a synthetic or natural refractory inorganic oxide used ordinarily as a binder for zeolite catalysts, such as silica, alumina, silica-alumina, kaolin, or silica-magnesium, molding the mixture into the desired shape, and then calcining the molded product. Advantageously, the amount of the zeolite in the molded product is generally 1 to 100% by weight, preferably 10 to 90% by weight, based on the weight of the molded product.

Prior to use, the catalyst so prepared may be treated at a temperature of 200° to 600° C., preferably 250° to 550° C., in a reducing atmosphere such as hydrogen gas.

(1) Isomerization

The zeolite of this invention can be advantageously used as a catalyst for isomerizing alkylbenzenes and alkylnaphthalenes, for example dialkylbenzenes such as xylenes, methylethylbenzenes and diethylbenzene, trialkylbenzenes such as trimethylbenzene and ethylxylenes, and dialkylnaphthalenes such as dimethylnaphthalenes. More specifically, it is suitable for use as a catalyst in the isomerization of an isomeric mixture of xylenes not in a thermodynamically equilibrium state, isomerization of an isomeric mixture of trimethylbenzenes not in a thermodynamically equilibrium state, isomerization of m-xylene to p-xylene, isomerization of 1,3,5-trimethylbenzene to 1,2,4-trimethylbenzene, isomerization of 1,6-dimethylnaphthalene to 2,6-dimethylnaphthalene, isomerization of 2,7-dimethylnaphthalene to 2,6-dimethylnaphthalene, isomerization of 2,3-dimethylnaphthalene to 2,6- or 2,7-dimethylnaphthalene.

In particular, the zeolite of this invention is characteristic in that it shows unique reactivity not found in conventional catalysts in the isomerization reaction of dialkylnaphthalenes. It has previously been thought that in the isomerization of a dialkylnaphthalene, only the shift of the alkyl group from the α-position to the β-position or from the β-position to the α-position on the same ring is possible. It has now been found in accordance with this invention that the use of the zeolite of this invention makes it possible to shift the alkyl substituent from one ring to another (for example, from the 3-position to the 6- or 7-position) and shift the alkyl substituent from the α-position (1-position) to the α-position (4-position) or from the β-position (2-position) to the β-position (3-position) on the same ring. The zeolite of this invention can thus be used advantageously as a catalyst for a reaction of converting 2,7-dimethylnaphthalene having little availability to 2,6-dimethylnaphthalene which is industrially valuable, or a reaction of isomerizing 2,3-dimethylnaphthalene into 2,6- or 2,7-dimethylnaphthalene.

The isomerization reaction can be carried out by contacting an alkylbenzene or alkylnaphthalene with a bed of the zeolite of the invention at a temperature generally in the range of 250° to 500° C., preferably 300° to 400° C. The weight hourly space velocity (WHSV) in this catalytic reaction can be varied according to the type of the starting material to be fed. In the case of alkylbenzenes which have a relatively small molecular size, the WHSV can be in the range of 1 to 100, preferably 5 to 40, based on the zeolite. In the case of alkylnaphthalenes having a relatively large molecular size, the time of contact of the alkylnaphthalenes with the zeolite is advantageously prolonged by adjusting WHSV to a range of 0.05 to 20, preferably 0.1 to 5, based on the zeolite.

The isomerization reaction can be performed generally at atmospheric pressure to 20 kg/cm$^2$.G, preferably 1 to 10 kg/cm$^2$.G. A diluent such as nitrogen or hydrogen may be supplied to the feedstock. Supplying of hydrogen is advantageous industrially because it will prolong the life of the catalyst activity. The suitable amount of hydrogen used in this case is 0.1 to 100 moles, preferably 1 to 50 moles, per mole of the feedstock.

In performing the isomerization reaction, the contacting of the feedstock with the catalyst may be effected in a fixed bed or fluidized bed reactor. Preferably, the former is used.

The isomerization reaction may be carried out either in the liquid phase or in the vapor phase.

(2) Transalkylation

Transalkylation is a reaction of shifting the alkyl group between two molecules of the same or different types of alkylbenzenes or alkylnaphthalenes. Specifically, the following reaction of shifting the methyl group can be cited as an example.

Toluene, a mixture of toluene and trimethylbenzenes, monomethylnaphthalene or a mixture of naphthalene and dimethylnaphthalenes used in the transalkylation reaction needs not to be pure, and may be diluted with other inert aromatic hydrocarbons and used as feedstocks. For example, a mixture of toluene and trimethylbenzenes so diluted suitably contains at least 10% by weight, preferably at least 30% by weight, of toluene, and at least 15% by weight, preferably at least 40% by weight, of trimethylbenzenes.

In performing the transalkylation reaction using the zeolite of this invention, the feedstock is passed through a catalyst bed composed of the zeolite of this invention at a temperature of generally 250° to 550° C., preferably 300° to 450° C. WHSV in this reaction may be varied depending upon the kind of the feedstock. In the case of alkylbenzenes having relatively low bulkiness in its molecular size, WHSV may be in the range of 0.1 to 50, preferably 0.5 to 10, based on the zeolite. In the case of relatively bulky alkylnaphthalenes, WHSV is suitably in the range of 0.05 to 20, preferably 0.1 to 5, based on the zeolite.

The transalkylation reaction may be carried out at atmospheric pressure to 20 kg/cm².G, preferably 1 to 10 kg/cm².G. A diluent such as nitrogen or hydrogen may be supplied to the feedstock. Supplying of hydrogen is advantageous industrially because it will prolong the life of the catalyst activity. The suitable amount of hydrogen used in this case is 0.1 to 100 moles, preferably 1 to 50 moles, per mole of the feedstock.

In performing the transalkylation reaction, the contacting of the feedstock with the catalyst may be effected in a fixed or fluidized bed reactor. Preferably, the former is used.

In the aforesaid isomerization reaction and transalkylation reaction catalyzed by the zeolite of the present invention, the zeolite shows much higher activity and selectivity than in the same reactions on conventional catalysts. Hence, the amount of the zeolite catalyst can be decreased and milder reaction conditions can be used. The industrial advantage of using the zeolite of the invention is great.

The following Examples illustrate the present invention in detail.

EXAMPLE 1

Five ZSM-5 zeolites having different silica-alumina mole ratios were synthesized by the method disclosed in U.S. Pat. No. 3,766,093. Tri-n-propylamine and n-propyl bromide were added as an organic cation source. Each of the synthetic zeolites was filtered, washed fully with decationized water, dried in an electric oven at 100° C. for 16 hours and then at 200° C. for 8 hours, and further calcined at 500° C. for 16 hours in an electric furnace while flowing air.

The synthetic zeolites had a silica-alumina mole ratio of 32.8 (to be referred to as "zeolite A"), 50.1 (to be referred to as "zeolite B"), 71.9 (to be referred to as "zeolite C"), 181 (to be referred to as "zeolite D"), and 270 (to be referred to as "zeolite E").

EXAMPLE 2

Preparation of zeolites in the invention:

(a) Twenty grams of the zeolite A obtained in Example 1 was suspended in 120 ml of a 5% by weight aqueous solution of sodium hydroxide, and the suspension was maintained for 5 hours under reflux. The residue in the flask was filtered, fully washed with decationized water, and dried at 100° C. for 16 hours in an electric oven. The weight of the dried product measured was 11.2 g. Its silica-alumina mole ratio decreased to 17.6 compared with that of zeolite A (to be referred to as "zeolite A-1").

The X-ray diffraction pattern of the zeolite A-1 obtained under Cu-K$_\alpha$ radiation mostly resembled that of the ZSM-5 disclosed in U.S. Pat. No. 3,702,886. In the zeolite A-1 obtained by the present invention, the strongest peaks at d(Å)=3.85 (2θ=23.14) evidently separated into d(Å)=3.86 (2θ=23.05) and d(Å)=3.83 (2θ=23.25).

(b) Ten grams of the zeolite A obtained in Example 1 was suspended in 40 ml of a 5% by weight aqueous solution of sodium hydroxide. In an autoclave, the suspension was stirred at 180° C. for 6 hours. After cooling, the contents were filtered, washed fully with decationized water, and dried in an electric oven at 100° C. for 16 hours. The weight of the product recovered was 6.3 g, and its silica-alumina mole ratio was 20.0 (the zeolite will be referred to as "zeolite A-2"). The X-ray diffraction pattern of this product had the characteristics shown in Table A given hereinabove.

(c) Ten grams of zeolite A was suspended in 50 ml of a 5% by weight aqueous solution of sodium hydroxide. Otherwise, by the same method as in section (b) above, "zeolite A-3" was obtained. The amount of the zeolite recovered was 5.6 g, and it had a silica/alumina mole ratio of 17.6. The X-ray diffraction pattern of zeolite A-3 had the characteristics shown in Table A hereinabove.

(d) Twenty grams of each of zeolite C, zeolite D and zeolite E obtained in Example 1 was treated under the same conditions and by the same method as in section (a) above. Thus, "Zeolite C-1", "zeolite D-1", and "zeolite E-1" were obtained. The amounts of these zeolites recovered were 11.2 g, 5.1 g, and 4.0 g, respectively. They had a silica/alumina mole ratio of 39.2, 44.6, 52.7, respectively. The X-ray diffraction patterns of these zeolites had the characteristics shown in Table A.

EXAMPLE 3

Each of zeolites A, C, E, A-1, A-2, A-3, C-1, D-1 and E-1 was molded into a size of 10 to 20 mesh, and calcined in an electric muffle furnace at 450° C. for 8 hours. About 0.5 g of the calcined zeolite was placed on a spring balance subpended in an adsorption tube, and the weight of the zeolite was precisely determined from the extension of the spring. The inside of the adsorption tube was then evacuated, and cyclohexane or n-hexane filled in a gas holder was introduced until the pressure inside the adsorption tube reached 60±2 mmHg. After standing at 20° C.±1° C. for 2 hours, the length of the spring balance was measured, and the amount of cyclohexane or n-hexane adsorbed was calculated from the extension of the spring balance. The amount of the substances adsorbed to the zeolite is calculated from the following formula.

$$V = \frac{W_2 - W_1}{W_1} \times 100$$

V is the amount (% by weight) of the substance adsorbed to the zeolite per unit weight of the zeolite. $W_1$ and $W_2$ represent the weights of the zeolite before and after adsorption, respectively.

Table 1 summarizes the amount of cyclohexane and n-hexane adsorbed ($V_{C-H}$, $V_{n-H}$) and the C.N.A. value defined by $C_{C-H}/V_{n-H}$.

TABLE 1

| Zeolite | SiO2/Al2O3 mole ratio | $V_{n-H}$ (wt. %) | $V_{C-H}$ (wt. %) | C.N.A. value |
|---|---|---|---|---|
| A | 32.8 | 10.3 | 7.0 | 0.68 |
| C | 71.9 | 9.9 | 6.3 | 0.64 |
| E | 270 | 9.5 | 6.2 | 0.65 |
| A-1 | 17.6 | 9.4 | 7.4 | 0.79 |
| A-2 | 20.0 | 4.1 | 3.7 | 0.91 |
| A-3 | 17.6 | 1.4 | 1.2 | 0.86 |
| C-1 | 39.2 | 6.8 | 6.3 | 0.93 |
| D-1 | 44.6 | 7.8 | 6.3 | 0.81 |
| E-1 | 52.7 | 10.3 | 10.8 | 1.05 |

The zeolites A-1 to E-1 obtained by treating ZSM-5 with an aqueous solution of sodium hydroxide had an increased C.N.A. value. This shows that steric hindrance against bulky molecules such as cyclohexane was reduced in the zeolites.

EXAMPLE 4

The powdery zeolites, A, B, C, D, E, A-1, A-2, A-3, C-1, D-1 and E-1 were obtained in Examples 1 and 2 were each converted to H-form zeolites.

Specifically, each zeolite was subjected to ion exchange at 70° C. for 16 hours using 5 ml, per unit weight of zeolite, of a 5% by weight aqueous solution of ammonium chloride, and this operation was performed twice. Then, the ion-exchanged zeolite was fully washed with water, dried in an electric dryer at 100° C. for 16 hours and then at 200° C. for 8 hours, and further calcined at 450° C. for 16 hours in an atmosphere of air in an electric muffle furnace. Analysis of the sodium content of the zeolite showed that in the zeolite after being subjected to the aforesaid procedure, more than 90% of its cation sites were occupied by protons.

The H-form zeolite so obtained was mixed fully with chromatographic alumina gel (smaller than 300 mesh) in a weight ratio of 1:1, and the mixture was molded into a size of 10 to 20 mesh. The molded article was calcined in an electric muffle furnace at 450° C. for 8 hours in an atmosphere of air, and 4 g of the calcined product was filled in a fixed bed-type reaction tube kept at atmospheric pressure. The temperature of the catalyst bed was adjusted to 350° C., and then 8 g/hr of cyclohexane and hydrogen (hydrogen/cyclohexane mole ratio=2/1) were fed into the reaction tube. Thus, the cyclohexane decomposition index was examined.

Figure 2:
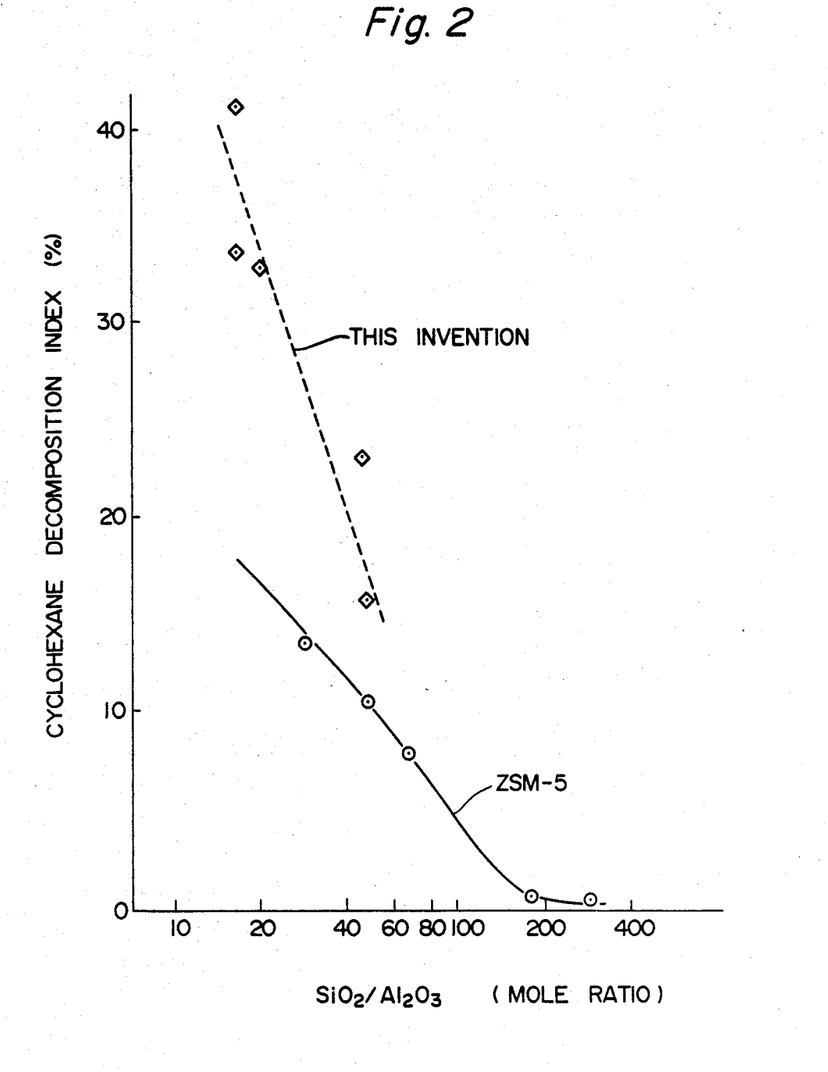
FIG. 2 is a graph obtained by plotting the correlation between the $SiO_2/Al_2O_3$ mole ratio and the cyclohexane decomposition index of the zeolite obtained in Examples 1 and 2 given hereinafter.

The cyclohexane decomposition index ratios (C.D.R. values) of the zeolites are shown in Table 2. The cyclohexane decomposition index of ZSM-5 having an arbitrary silica/alumina mole ratio, which serves as a standard, was determined from the correlation between the silica/alumina mole ratio and the cyclohexane decomposition index in the catalysts obtained in Example 1. FIG. 2 gives this correlation, and indicates that the cyclohexane decomposition ratio of the zeolite of this invention shown by the broken line is higher than that of ZSM-5 shown by the solid line. It is clearly seen from Table 2 that the zeolites of this invention have a C.D.R. ratio well over 1.

TABLE 2

| Zeolite | SiO2/Al2O3 mole ratio | Cyclohexanone decomposition index (%) | C.D.R. |
|---|---|---|---|
| A-1 | 17.6 | 40.5 | 2.0 |
| A-2 | 20.0 | 33.3 | 1.8 |
| A-3 | 17.6 | 34.0 | 1.7 |
| C-1 | 39.2 | 21.1 | 1.8 |
| D-1 | 44.6 | 23.5 | 2.1 |
| E-1 | 52.7 | 15.7 | 1.6 |

EXAMPLE 5

In this example, transalkylation was carried out for obtaining xylene from toluene and 1,2,4-trimethylbenzene using the zeolite C-1 of this invention (silica/alumina mole ratio=39.2) and the zeolite A as a comparison (silica/alumina mole ratio=32.8).

Each of these zeolites was converted to H-form zeolite by the same method as described in Example 4, and fully mixed with chromatographic alumina gel (smaller than 300 mesh) in a weight ratio of 1:1. The mixture was molded into a size of 10 to 20 mesh, and calcined in an electric muffle furnace at 450° C. for 8 hours. Five grams of the calcined zeolite was filled in a fixed bed reaction tube kept under atmospheric pressure. The temperature of the catalyst bed was adjusted to 400° C., and 10 g of a mixture of toluene and 1,2,4-trimethylbenzene in a mole ratio of 1:1 and hydrogen (hydrogen/hydrocarbon mole ratio=1/1) were fed into the reaction tube.

Five hours after the start of feeding of the starting mixture, the product had the composition shown in Table 3.

It is seen that in spite of having higher silica/alumina mole ratio than zeolite A, the zeolite C-1 of this invention gives a very large amount of xylene and is therefore effective for transalkylation reaction.

TABLE 3

|  | Feed | Product with zeolite C-1 | Product with zeolite A |
|---|---|---|---|
| Composition (wt. %) | | | |
| C$_5$-paraffin | | 0.7 | 0.6 |
| Benzene | | 3.1 | 1.2 |
| Toluene | 43.4 | 27.3 | 36.9 |
| Xylenes | | 30.6 | 15.2 |
| Trimethylbenzenes | 56.6 | 37.3 | 45.0 |
| C$_{10}$+ aromatics | | 1.0 | 1.1 |
| Conversion of toluene (%) | | 37.1 | 14.9 |
| Conversion of trimethylbenzenes (%) | | 34.0 | 20.5 |
| Yield of xylenes (%) | | 86.0 | 85.5 |

In the above table, the conversion of toluene, the conversion of trimethylbenzenes and the yield of xylenes are defined as follows:

$$\text{Conversion of toluene (\%)} = \frac{\left(\begin{array}{c}\text{Concentration}\\\text{of toluene in}\\\text{the feed}\end{array}\right) - \left(\begin{array}{c}\text{Concentration}\\\text{of toluene in}\\\text{the product}\end{array}\right)}{\text{Concentration of toluene in the feed}} \times 100$$

$$\text{Conversion of trimethyl-benzenes (\%)} = \frac{\left(\begin{array}{c}\text{Concentration}\\\text{of trimethyl-}\\\text{benzenes in}\\\text{the feed}\end{array}\right) - \left(\begin{array}{c}\text{Concentration}\\\text{of trimethyl-}\\\text{benzenes in}\\\text{the product}\end{array}\right)}{\text{Concentration of trimethylbenzenes in the feed}} \times 100$$

$$\text{Yield of xylenes (\%)} = \frac{\text{Moles of xylene formed}}{\left(\begin{array}{c}\text{Moles of}\\\text{toluene}\\\text{consumed}\end{array}\right) + \left(\begin{array}{c}\text{Moles of}\\\text{trimethylbenzenes}\\\text{consumed}\end{array}\right)} \times 100$$

EXAMPLE 6

In this Example, a reaction was carried out for synthesizing monomethylnaphthalene from naphthalene and dimethylnaphthalenes using zeolite A-2 (silica/alumina mole ratio=20.0).

Specifically, H-form zeolite of A-2 was molded and calcined in the manner shown in Example 5. The grams of the calcined zeolite was filled in a fixed bed reaction tube. The temperature of the catalyst bed was adjusted to 370° C., and 5 g of a starting mixture consisting of naphthalene/dimethylnaphthalenes isomeric mixture in a mole ratio of 1/1 and hydrogen (hydrogen/hydrocarbon mole ratio=3/1) were fed into the reaction tube.

One hour after the start of feeding of the starting material, the product had the composition shown in Table 4.

Marked formation of monomethylnaphthalene was noted in this reaction.

TABLE 4

|  | Feed | Product |
|---|---|---|
| Composition (wt. %) | | |
| Naphthalene | 45.1 | 32.8 |
| Monomethylnaphthalenes | | 27.0 |
| Dimethylnaphthalenes | 54.9 | 38.1 |
| Trimethylnaphthalenes | | 2.1 |
| Conversion of naphthalene (%) | | 27.3 |
| Conversion of dimethylnaphthalenes (%) | | 30.6 |
| Yield of methylnaphthalenes (%) | | 93.3 |

In the above table, the conversion of naphthalene, the conversion of dimethylnaphthalenes and the yield of methylnaphthalenes are as defined below.

$$\text{Conversion of naphthalene (\%)} = \frac{\left(\begin{array}{c}\text{Concentration}\\\text{of naphthalene}\\\text{in the feed}\end{array}\right) - \left(\begin{array}{c}\text{Concentration}\\\text{of naphthalene}\\\text{in the product}\end{array}\right)}{\text{Concentration of naphthalene in the feed}} \times 100$$

$$\text{Conversion of dimethylnaph-thalenes (\%)} = \frac{\left(\begin{array}{c}\text{Concentration}\\\text{of dimethyl-}\\\text{naphthalenes}\\\text{in the feed}\end{array}\right) - \left(\begin{array}{c}\text{Concentration}\\\text{of dimethyl-}\\\text{naphthalenes}\\\text{in the product}\end{array}\right)}{\text{Concentration of diemthylnaphthalene in the feed}} \times 100$$

$$\text{Yield of methyl-naphthalenes (\%)} = \frac{\text{Moles of methylnaphthalenes formed}}{\left(\begin{array}{c}\text{Moles of}\\\text{naphthalene}\\\text{consumed}\end{array}\right) + \left(\begin{array}{c}\text{Moles of di-}\\\text{methylnaphthalene}\\\text{consumed}\end{array}\right)} \times 100$$

EXAMPLE 7

In this example, dimethylnaphthalenes were isomerized using zeolite A-3 (silica/alumina mole ratio=17.6).

Specifically, H-form zeolite of A-3 was molded and calcined in the manner described in Example 5, and 10 g of the calcined zeolite was filled in a fixed bed reaction tube. The temperature of the catalyst bed was adjusted to 310° C., and 5 g of a dimethylnaphthalenes mixture containing 1,6-dimethylnaphthalene as a main component and hydrogen (hydrogen/dimethylnaphthalenes mole ratio=3/1) were fed into the reaction tube. One hour after the start of feeding of the starting mixture, the product had the composition shown in Table 5.

It is seen that in this reaction, the methyl group shifted from the α-position (1-position) to the β-position (2-position) to give 2,6-dimethylnaphthalene, and also the methyl group shifted from the β-position (6-position) to the β-position (7-position) to give 2,7-dimethylnaphthalene.

TABLE 5

|  | Feed (wt. %) | Product (wt. %) |
|---|---|---|
| Monomethylnaphthalenes | — | 2.70 |
| 2,6-Dimethylnaphthalene | 8.54 | 27.19 |
| 1,6-Dimethylnaphthalene | 71.38 | 26.22 |
| 2,3-Dimethylnaphthalene | 0.01 | 2.12 |
| 2,7-Dimethylnaphthalene | 0.50 | 15.88 |
| Other dimethylnaphthalenes | 19.11 | 23.38 |
| Trimethylnaphthalenes | 0.46 | 2.52 |

EXAMPLE 8

In this example, 2,3-dimethylnaphthalene was isomerized in the liquid phase using the same catalyst as in Example 7.

A mini-autoclave was charged with 1 g of powdery H-form zeolite of A-3 and 4 g of 2,3-dimethylnaphthalene (commercially available special reagent grade). After maintaining the mixture at 350° C. for 7 hours, the composition of the product was analyzed. It was found that the product contained 10.5% of 2,6-dimethylnaphthalene and 7.5% of 2,7-dimethylnaphthalene.

This shows that one of the two methyl groups on the same ring intramolecularly shifted to another ring.

EXAMPLE 9

In this example, 1,3,5-trimethylbenzene was isomerized using the same molded catalyst as described in Example 5.

The reaction was carried out at a temperature of 400° C. and a WHSV of 2.0 hr$^{-1}$ (based on the weight of the catalyst) while maintaining the mole ratio of hydrogen/trimethylbenzene at 2/1. Two hours after the start of feeding the starting material, the composition of the product was analyzed. It was found that trimethylbenzenes contained 65% of a 1,2,4-isomer (pseudocumane).

EXAMPLE 10

The zeolite C-1 obtained in Example 2 (d) was subjected to ion exchange with an aqueous solution of ammonium chloride by the method described in Example 4 to obtain H-form zeolite. Two grams of the H-form zeolite was dipped in 10 ml of an aqueous solution containing 10.6 mg of chloroplatinic acid hexahydrate dissolved therein, and water was evaporated by using a rotary evaporator. The residue was dried in an electric oven at 100° C. for 8 hours and then at 200° C. for 16 hours, and then calcined in an electric muffle furnace at 450° C. for 8 hours under flowing of air to give a zeolite catalyst containing 0.2% of platinum.

The catalyst was molded and calcined by the method described in Example 5, and 4 g of the calcined catalyst was filled in a fixed bed reaction tube kept under atmospheric pressure. The temperature of the catalyst bed was elevated to 400° C. under flowing of nitrogen, and then hydrogen gas was passed through the catalyst bed to reduce platinum contained in the catalyst for 2 hours at this temperature. Then, the reaction temperature was maintained at 400° C., and 8 g of an alkylaromatic hydrocarbon material having the composition shown in Table 6 and hydrogen (hydrogen/aromatic hydrocarbon mole ratio=2/1) were fed into the reactor. The results are shown in Table 6. It is seen from Table 6 that the catalyst composition obtained by adding platinum to the zeolite induced transalkylation and dealkylation at the same time.

TABLE 6

| | Feed | Product |
|---|---|---|
| Composition (wt. %) | | |
| C$_5$⁻ paraffins | — | 6.43 |
| Benzene | 0.01 | 7.60 |
| Toluene | 55.81 | 48.77 |
| Xylenes | 1.30 | 20.64 |
| Trimethylbenzenes | 22.10 | 16.29 |
| Ethyltoluenes | 2.15 | 0.05 |
| Diethylbenzenes | 8.71 | 0.01 |
| Ethylxylenes | 9.68 | 0.15 |
| Durene, etc. | 0.24 | 0.06 |
| Conversion of toluene (%) | | 12.6 |
| Conversion of trimethylbenzenes (%) | | 26.3 |
| Conversion of ethyltoluenes (%) | | 97.7 |
| Conversion of diethylbenzenes (%) | | 99.9 |
| Conversion of ethylxylenes (%) | | 98.5 |

In the above table, the conversion of each feed component is defined as follows:

$$\text{Conversion (\%)} = \frac{\left(\begin{array}{c}\text{Concentration of}\\\text{the component}\\\text{in the feed}\end{array}\right) - \left(\begin{array}{c}\text{Concentration of}\\\text{the component}\\\text{in the product}\end{array}\right)}{\text{Concentration of the component in the feed}} \times 100$$

What we claim is:

1. A crystalline aluminosilicate zeolite characterized by having
   (a) a silica/alumina mole ratio in the range of from 10 to 100,
   (b) X-ray lattice distances d shown in Table A in the specification,
   (c) a (cyclohexane/n-hexane) adsorption ratio of at least 0.7, and
   (d) when the intensity ($I_o$) of the X-ray diffraction peak at d(Å)=3.86 is taken as 100, the relative intensity ($I/I_o$) of the X-ray diffraction peak d(Å)=3.83 is at least 75.

2. The zeolite of claim 1 wherein the silica/alumina mole ratio is in the range of from 15 to 70.

3. The zeolite of claim 1 wherein the (cyclohexane/n-hexane) adsorption ratio is at least 0.8.

4. The zeolite of claim 1 which has a cyclohexane decomposition index ratio, in the activated state, of at least 1.1.

5. The zeolite of claim 4 wherein the cyclohexane decomposition index ratio is at least 1.5.

6. A process for producing the zeolite of claim 1, which comprises heating a crystalline aluminosilicate zeolite ZSM-5 having a silica/alumina mole ratio of from 20 to 300 at a temperature between 80° C. and 250° C. in an aqueous solution containing 0.1 to 1 g, per gram of the ZSM-5 zeolite, of an alkali metal hydroxide.

7. The process of claim 6 wherein the alkali metal hydroxide is sodium hydroxide.

8. The process of claim 6 wherein the heating is carried out until the weight ratio of the formed zeolite to the starting zeolite ZSM-5 is in the range of from 10 to 80.

9. The process of claim 6 wherein the alkali metal hydroxide is used in the amount of 0.2 to 0.7 g per gram of the zeolite ZSM-5.

* * * * *